US006331319B1

(12) United States Patent
Badylak et al.

(10) Patent No.: US 6,331,319 B1
(45) Date of Patent: Dec. 18, 2001

(54) GALACTOSIDASE MODIFIED SUBMUCOSAL TISSUE

(75) Inventors: Stephen F. Badylak, West Lafayette; Rae Denese Record, Lafayette, both of IN (US); Timothy B. McPherson, Columbia, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/463,937

(22) PCT Filed: Sep. 11, 1998

(86) PCT No.: PCT/US98/18956

§ 371 Date: Feb. 2, 2000

§ 102(e) Date: Feb. 2, 2000

(87) PCT Pub. No.: WO99/12555

PCT Pub. Date: Mar. 18, 1999

Related U.S. Application Data

(60) Provisional application No. 60/058,545, filed on Sep. 11, 1997.

(51) Int. Cl.[7] .................................................. A61K 35/38
(52) U.S. Cl. ............................................................ 424/551
(58) Field of Search ............................................... 424/551

(56) References Cited

U.S. PATENT DOCUMENTS

| 5,275,826 | 1/1994 | Badylak et al. ..................... 424/551 |
| 5,922,027 | 7/1999 | Stone ................................ 623/16.11 |

FOREIGN PATENT DOCUMENTS

| WO 96/24365 | 8/1996 | (WO) . |
| WO 96/31232 | 10/1996 | (WO) . |

OTHER PUBLICATIONS

"Glucosaminoglycan Content of Small Intestinal Submucosa: A Bioscaffold for Tissue Replacement" by Jason P. Hodde, Stephen F. Badylak, Andrew O. Brightman, and Sherry L. Voytik–Harbin; Tissue Engineering (1996) vol. 2, No. 3, 209–217.

*Primary Examiner*—Jean C. Witz
(74) *Attorney, Agent, or Firm*—Barnes & Thornburg

(57) ABSTRACT

A tissue graft composition comprising submucosal tissue that has been enzymatically treated with galactosidase is described. The galactosidase modified submucosal tissue can be implanted to replace or support damaged or diseased tissues or utilized to form a cell culture growth substrate.

7 Claims, No Drawings

US 6,331,319 B1

GALACTOSIDASE MODIFIED SUBMUCOSAL TISSUE

CROSS-REFERENCE TO RELATED APPLICATIONS

This application is a U.S. national application of international application Ser. No. PCT/US98/18956 filed Sep. 11, 1998, which claims priority to U.S. provisional application serial No. 60/058,545 filed Sep. 11, 1997.

FIELD OF THE INVENTION

The present invention relates to enzymatically treated submucosal tissue and methods for its preparation and use. More particularly, the present invention is directed to submucosal tissue that is at least partially digested with galactosidase.

BACKGROUND OF THE INVENTION

It is known that compositions comprising the tunica submucosa of the intestine of warm-blooded vertebrates can be used advantageously as tissue graft materials. See U.S. Pat. Nos. 4,902,508 and 5,281,422, the disclosures of which are expressly incorporated herein by reference. The tissue graft compositions described in those patents are characterized by excellent mechanical properties, including high compliance, a high burst pressure point, and an effective porosity index which allows such compositions to be used beneficially for vascular graft and connective tissue graft constructs. When used in such applications the graft constructs appear not only to serve as a matrix for the regrowth of the tissues replaced by the graft constructs, but, indeed, to promote or induce such regrowth of endogenous tissue. Common events to this remodeling process include widespread and rapid neovascularization, proliferation of granulation mesenchymal cells, biodegradation/resorption of implanted intestinal submucosal tissue material, and lack of immune rejection.

It is also known that intestinal submucosa can be fluidized by comminuting and/or enzymatic digestion, without loss of its apparent biotropic properties, for use in less invasive methods of administration (e.g., by injection or topical application) to host tissues in need of repair. See U.S. Pat. No. 5,275,826, the disclosure of which is expressly incorporated herein by reference.

Submucosal tissue grafts have been successfully used as a xenograft in vascular, dura mater, urinary bladder, and orthopedic applications, and as dermal grafts. The remodeled tissue resembles the native tissue, both grossly and histologically, such that the original submucosal tissue graft is generally unidentifiable when remodeling is complete. Despite its xenogeneic nature, vertebrate submucosal tissue has not induced a clinical rejection response in the animal systems in which it has been tested, including rats, mice, dogs, cats, rabbits, and sheep. Thus, submucosal tissue is a potentially useful xenogeneic graft material for use in humans.

Galactosyl-α(1,3)galactose (referred to as the Gal epitope) is a glycosyl modification of cell surface components and some serum proteins in all mammals, except humans and Old World apes. The epitope comprises a terminal galactose moiety linked to another galactose moiety through an α1–3 linkage. It has been shown that human serum contains naturally occurring IgG and IgM antibodies directed against this epitope. It is estimated that 1% of all circulating IgG in humans is anti-Gal. This high level of anti- Gal epitope antibodies is thought to be produced in response to endogenous bacteria in the gastrointestinal system; the lipopolysaccharides of those bacteria contain the Gal epitope. Xenogeneic transplantation of organ tissue into a human host results in IgG and IgM antibodies binding to the Gal epitope (especially for those epitopes located on endothelial cells), the initiation of an inflammatory reaction, and vascular thrombosis and hyperacute xenograft rejection of the transplant. Accordingly, a major obstacle to successful xenotransplantation of porcine and other non-Old World ape vertebrate species organs into humans is the presence of Gal epitopes on the tissues of those organs.

As disclosed herein, the Gal epitope has also been found in porcine submucosal tissue prepared in accordance with the procedures disclosed in U.S. Pat. Nos. 4,902,508 and 5,281,422. It is not known whether the Gal epitope exists as a naturally occurring component of the submucosal tissue or whether the epitope is a remnant of cell lysis, and remains attached to the submucosal tissue during processing of the submucosal tissue.

There have been no reports of submucosal tissue graft constructs inducing an immune response after implantation in the animal systems in which it has been tested, including rats, mice, dogs, cats, rabbits, and sheep. However, due to the association of the Gal epitope with hyperacute xenograft whole organ transplant rejection in humans, a preferred submucosal tissue graft construct would comprise submucosal tissue substantially free of the Gal epitope.

SUMMARY OF THE INVENTION

The present invention is directed to submucosal tissue that has been treated with galactosidase to produce submucosal tissue substantially free of detectable amounts of the Gal epitope. Such "Gal free" submucosal tissue is used to form tissue graft constructs for the replacement and repair of damaged or diseased endogenous tissues.

DETAILED DESCRIPTION OF THE PREFERRED EMBODIMENTS

Definitions:

The term "Gal epitope" refers to a glycosyl modification [galactosyl-α(1,3)galactose] of cellular compounds present on the cell surface or on serum proteins of all mammals except humans and Old World apes.

The term "glycosidase" as use herein refers to an enzyme that cleaves/destroys the terminal a-linked galactose present on most vertebrate cellular components. For example one glycosidase useful in accordance with the present is α-galactosidase.

The term "glycosaminoglycanase" (GAGase) as use herein refers to an enzyme that hydrolyzes glycosaminoglycans (GAG) including, for example chondroitin sulfate, hyaluronic acid heparin and heparin sulfate.

The term "Gal free submucosal tissue" refers to submucosal tissue that is substantially free of all detectable amounts of the Gal epitope as determined by the antibody and lectin assays described in detail in Example 1.

The present invention is directed to warm blooded vertebrate submucosal tissue that is substantially free of the Gal epitope, and methods for its preparation and use. More particularly, the present invention is directed to submucosal tissue that has been at least partially digested with an enzyme, such as α-galactosidase, to diminish the level of the Gal epitope present in the submucosal tissue. The galactosidase treated submucosal tissue is used in accordance with the present invention as a non-immunogenic tissue graft composition and as an in vitro cell culture substrate.

The galactosidase treated submucosal tissue of the present invention is derived from vertebrate submucosa and comprises naturally associated extracellular matrix proteins, glycoproteins and other factors. Preferably the submucosal tissue comprises intestinal submucosa of a warm-blooded vertebrate, and one particularly preferred source of the submucosal tissue is the small intestine of warm-blooded vertebrates. Suitable submucosal tissue comprises the tunica submucosa delaminated from the tunica muscularis and at least the luminal portion of the tunica mucosa. In one preferred embodiment of the present invention the submucosal tissue is intestinal submucosa comprising the tunica submucosa and basilar portions of the tunica mucosa including the larnina muscularis mucosa and the stratum compactum which layers are known to vary in thickness and in definition dependent on the source vertebrate species. Submucosal tissue can also be prepared from other organs of vertebrate species, for example, from the urogenital system, including the urinary bladder (see U.S. Pat. No. 5,554,389), and other portions of the digestive tract including the stomach. The disclosures of U.S. Pat. No. 5,554,389 is expressly incorporated herein.

The preparation of submucosal tissue for use in accordance with this invention is described in U.S. Pat. Nos. 4,902,508 and 5,554,389. To sumrnmarize, submucosal tissue is prepared from vertebrate intestine (or other organ source), preferably harvested from porcine, ovine or bovine species, but not excluding other species, by subjecting the intestinal tissue to abrasion using a longitudinal wiping motion to remove the outer layers, comprising smooth muscle tissues, and the innermost layer, i.e., at least the luminal portion of the tunica mucosa. The submucosal tissue is rinsed with saline and optionally sterilized; it can be stored in a hydrated or dehydrated state. Lyophilized or air dried submucosal tissue can be rehydrated and used in accordance with this invention without significant loss of its cell proliferative activity.

Stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100 to about 200 micrometers, and consists primarily (greater than 98%) of a cellular, eosinophilic staining (H&E stain) extracellular matrix material.

The submucosal tissue specified for use in accordance with this invention can also be in a fluidized form. Submucosal tissue can be fluidized by comminuting the tissue and optionally subjecting it to enzymatic digestion. The preparation of fluidized forms of submucosal tissue is described in U.S. Pat. No. 5,275,826, the disclosure of which is expressly incorporated herein by reference. Fluidized forms of submucosal tissue are prepared by comminuting submucosal tissue by tearing, cutting, grinding, or shearing the harvested submucosal tissue. In accordance with one embodiment, pieces of submucosal tissue are comminuted by shearing in a high speed blender, or by grinding the submucosa in a frozen or freeze-dried state to produce a powder that can thereafter be hydrated with water or a buffered saline to form a submucosal fluid of liquid, gel or paste-like consistency.

The native or fluidized submucosa formulation can be treated with an enzyme for a period of time sufficient to solubilize all or a major portion of the submucosal tissue components. Preferably submucosal tissue is digested with an enzyme that hydrolyzes the structural components of the submucosal tissue to produce a suspension or homogenous solution of submucosal tissue components. Submucosal tissue can be enzymatically treated with proteases (for example, a collagenase or trypsin or pepsin), glycosaminoglycanases or a combination of proteases and glycosaminoglycanases. Optionally, other appropriate enzymes (i.e. those that hydrolyze the structural components of the submucosal tissue without substantially adversely impacting the biotropic properties of the tissue) can be used alone or in combination with proteases and glycosaminoglycanases. The tissue digest can be optionally filtered to provide a homogenous solution of partially solubilized submucosal tissue.

The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.0.

The present invention also contemplates the use of powder forms of submucosal tissue. In one embodiment a powder form of submucosal tissue is prepared by pulverizing submucosal tissue under liquid nitrogen to produce particles ranging in size from 0.1 to 1 $mm^2$. The particulate composition is then lyophilized overnight and sterilized to form a solid substantially anhydrous particulate composite. Alternatively, a powder form of submucosal tissue can be formed from fluidized submucosal tissue by drying the suspensions or solutions of comrninuted submucosal tissue.

It is anticipated that each of the various forms of submucosal tissue (native, fluidized, protease or GAGase treated and powder forms) has the Gal epitope associated with the tissue. In accordance with the present invention, those various forms of submucosal tissue can be further modified to reduce the amount of Gal epitope present in the tissue. Alternatively, the native submucosal tissue can be first enzymatically treated to reduce the amount of Gal epitope present in the tissue before the tissue is fluidized, protease or GAGase treated, or formed into powder form. In one embodiment, native submucosal tissue is treated with α-galactosidase to produce a Gal epitope depleted submucosal tissue. In a preferred embodiment the submucosal tissue is hydrolyzed with α-galactosidase until it is substantially free of detectable amounts of the Gal epitope. The Gal free tissue can then optionally be further manipulated to produce the described fluidized, protease/GAGase treated, and powder forms of submucosal tissue.

As the experimental data of Example 1 indicate, the Gal epitope is associated with porcine submucosal tissue. The Gal epitope was detected in porcine submucosal tissue by immunohistochemical staining methods using both a naturally occurring lectin (IB-4) that binds to the Gal epitope and freshly collected pooled human serum as the source of primary antibodies. Pretreating the porcine submucosal tissue with human serum decreased the intensity of staining by the IB4 lectin, and pretreating the tissue with the IB-4 lectin decreased the intensity of antibody staining. Accordingly, both the IB-4 lectin and the pooled primary antibodies recognized the same site. α-Galactosidase treatment of the submucosal tissue effectively reduced staining with the lectin to negligible amounts, indicating that the Gal epitope could be cleaved from the submucosal tissue by treatment with α-galactosidase.

It is unknown whether the epitope exists as a naturally occurring component of the submucosal tissue extra cellular matrix or whether the epitope is a remnant of cell lysis and remains attached to the submucosal tissue extra cellular matrix during processing of the submucosal tissue. Since the Gal epitope has been detected on serum proteins, and thus is not exclusive to cell surfaces, the Gal epitope may be present on extracellular matrix proteins that comprise submucosal tissue. Additionally, since submucosal tissue preparation begins with mechanical delamination of the jejunum, which certainly results in the rupture of a significant number of cells, cellular components deposited during the preparation of submucosal tissue may also contribute to the presence of the epitope in the submucosal tissue.

As noted above the presence of the Gal epitope on nonhuman mammalian tissues has been an obstacle to xenograft transplantations due to hyperacute rejection of the xenograft. The association of the Gal epitope with porcine intestinal submucosal tissue raises the issue of whether submucosal tissue could activate complement in fresh human plasma thus leading to rejection or complement mediated destruction of the tissue upon implantation into humans. Hyperacute rejection results from complement activation, especially in the blood supply to the grafted organ. The complement system is a complex system of approximately 20 interacting components and is involved in antibody-mediated cell lysis of cells as well as stimulating phagocytic cells to ingest and destroy cells. Most of the components of the complement system are in an inactive form and are activated by a sequence of proteolytic activation reactions triggered by an immune response. In particular the complement cascade can be activated by antibody-antigen reaction, such as that between an anti-Gal antibody and the Gal epitope.

The pivotal component of the complement system proteolytic cascade is C3. C3 can be activated by two different pathways, the classical pathway and the alternative pathway, in both cases C3 is cleaved by an enzyme complex into C3a and C3b. C3b continues the cascade and C3a is involved in anaphylaxis, chemotaxes, and acute inflammation. A radio-immunoassay kit to measure C3a is commercially available (Amersham) and can be utilized as an indicator of complement activation. This kit was used to determine if submucosal tissue induces complement activation in human plasma (See Example 2). Based on the results of this assay, sheets of porcine submucosal tissue prepared in accordance with the present invention do not activate complement, despite the presence of immunologically detectable Gal epitopes.

The fact that submucosal tissue does not stimulate complement activation is surprising, considering the strongly positive staining observed with the HB-4 lectin and human serum. This suggests that naturally occurring human IgG and IgM bind to the submucosal tissue, but fail to fix complement significantly in vitro. Complement activation requires binding of IgG or IgM to the antigen in relatively high density. Accordingly, the lack of iii vitro complement response may result from a low density of the Gal epitopes in the tissue. Furthermore, IgG/antigen complexes activate complement less efficiently than IgM/antigen complexes, especially at low antigen densities, and the competition of IgG for binding with the Gal epitope may also contribute to the low complement response. Finally, the process of cryo-sectioning and fixing may expose more antigenic sites for immunoperoxidase labeling than are available in the native tissue, resulting in impressive immunoperoxidase staining despite the poor complement activation. In particular the pore size and distribution of the pores in the native submucosal tissue may restrict complement access to only the most superficial structures, effectively decreasing the amount of antigen available for binding to the antigen.

Regardless of porcine submucosal tissue's ability to activate complement in vitro upon exposure to human serum, due to the association of the Gal epitope with hyperacute xenograft whole organ transplant rejection in humans, a preferred graft construct would comprise a tissue substantially free of the Gal epitope. Gal free submucosal tissue can be prepared in accordance with the present invention by contacting the submucosal tissue with an enzymatic solution wherein the enzyme destroys or separates the Gal epitope from the submucosal tissue. Preferably the enzyme is α-galactosidase.

Submucosal tissue treated to remove the Gal epitope can be in its native state, or in a fluidized, suspension, solution or powdered forms. The tissue is contacted with the enzyme under conditions (including temperature, pH, salt concentration, etc) suitable for enzymatic activity. The digestion is conducted for a time sufficient to reduce the Gal epitope content of the tissue. Preferably, the Gal epitope concentration associated with the tissue is reduced by greater than 50%, more preferably Gal epitope concentration is reduced by greater than 90% and in accordance with one embodiment vertebrate submucosal tissue is enzymatically treated to be substantially free of detectable amounts of the Gal epitope. After the tissue has been enzymatically digested to deplete the Gal epitope content, the tissue is repeatedly washed in saline or a suitable buffered solution to remove the cleaved epitope and the enzyme. Alternatively, after enzymatic digestion to deplete Gal epitope content, the tissue can be dialyzed against a buffered solution to remove the cleaved epitope and enzyme.

The length of time the submucosal tissue is digested with the enzyme is dependent on the amount of tissue to be treated relative to the concentration of the enzyme (assuming environmental factors such as temperature, pH, salt concentration, etc have been optimized for enzymatic activity). One preferred group of enzymes utilized for depleting the Gal epitope content of submucosal tissue includes galactosidases, including particularly the use of α-galactosidase, either alone or in combination with other galactosidases or other enzymes.

In accordance with one embodiment the submucosal tissue is treated with α-galactosidase at a concentration ranging from about 5 to about 100 units/ml, and more preferably about 10 to about 50 units/ml for 6–12 hours. Each digestion reaction typically comprises approximately about 10 to about 100 mg of submucosal tissue, and more preferably about 40 to about 60 mg of submucosal tissue. Accordingly, about 0.2 to about 5 units of enzyme are added per 1 mg of submucosal tissue, and more preferably about 0.25 to about 2 units of enzyme are added per 1 mg of submucosal tissue and the tissue is incubated at 37° C. for 6–12 hours. In one embodiment, 20 units/ml of α-galactosidase are added to the submucosal tissue and the tissue is digested for 8 to 10 hours at 37° C. The submucosal tissue can be fluidized or partially dehydrated prior to contact with the solution containing one or more galactosidases to assist enzymatic digestion of the Gal epitopes.

In one embodiment a Gal free tissue graft construct comprising intestinal submucosa delaminated from the tunica muscularis and at least the luminal portion of the tunica mucosa of vertebrate intestine is prepared by contacting the tissue with galactosidase for a sufficient amount of time to remove substantially all of the Gal epitope. For larger pieces of submucosal tissue, the tissue can be dehydrated or perforated before being contacted with the galactosidase solution to enhance access of the enzyme to the Gal epitope present in the tissue and decrease the time of digestion. In another embodiment fluidized forms of the Gal free submucosal tissue (including enzymatically digested suspensions and solutions of submucosal tissue) are treated to remove the Gal epitope and are then gelled to form a solid or semi-solid matrix.

Enzymatic digestion of the submucosal tissue to remove the Gal epitope can be accomplished without loss of the biotropic properties of the native submucosal tissue. It has been previously reported that submucosal tissue can be utilized as a cell culture substrate (see U.S. Pat. No. 5,695,998, the disclosure of which is expressly incorporated herein). As demonstrated by the data of Example 3, Gal free submucosal tissue exhibits similar properties as a cell culture substrate, with regards to cell proliferation and differentiation its vitro, as native submucosal tissue. Accordingly, the removal of the Gal epitope does not appear to affect submucosal tissue's ability to stimulate the growth and differentiation of cells, and therefore, the Gal free submucosal tissue can be utilized in tissue graft compositions to stimulate the repair of damaged or diseased tissues.

In accordance with the present invention, the Gal free submucosal tissue compositions of the present invention are used advantageously to induce the formation of endogenous tissue at a desired site in a warm blooded vertebrate. The method comprises the step of contacting the damaged or diseased site with a graft composition comprising Gal free submucosal tissue in an amount effective to induce endogenous tissue growth at the site the composition is administered. The Gal free submucosal tissue compositions can be administered to the host in either solid or sheet form, by surgical implantation, or in fluidized form, by injection.

In particular, the Gal free submucosal tissue compositions of the present invention lend themselves to a wide variety of surgical applications relating to the repair or replacement of damaged tissues, including, for example the repair of vascular and connective tissues. Connective tissues for the purposes of the present invention include bone, cartilage, muscle, tendons, ligaments, and fibrous tissue including the dermal layer of skin. The use of the Gal free submucosal tissue segments in the repair or replacement of connective tissues can be conducted using the same procedures described in U.S. Pat. Nos. 5,281,422 and 5,352,463, expressly incorporated herein by reference. Furthermore, it is anticipated that Gal free submucosal tissue graft constructs will have utility in the replacement and repair of vascular, neural, dura mater, urinary bladder, and dermal tissues.

The present Gal free submucosal tissue composition may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the graft is preferably used. For instance, it is believed that strong gamma radiation may cause loss of strength in the graft material. Because one of the most attractive the present intestinal submucosa grafts is their ability to induce host-remodeling responses, it is desirable not to use a sterilization approach which will detract from that property. Preferred sterilization techniques include exposing the graft to peracetic acid, low dose gamma irradiation and gas plasma sterilization; peracetic acid sterilization being the most preferred method. Typically, after the tissue graft composition has been sterilized, the composition is wrapped in a porous plastic wrap and sterilized again using electron beam or gamma irradiation sterilization techniques.

Gal free submucosal tissue can also be used in accordance with this invention as a cell growth substrate in a variety of forms, including its native sheet-like configuration, as a gel matrix, as a supplemental component in art-recognized cell/tissue culture media, or as coating for culture-ware to provide a more physiologically relevant substrate that supports and enhances the proliferation of cells in contact with the submucosal matrix. The composition comprises submucosal tissue that has been fluidized by enzymatically digesting the tissue with an enzyme selected from the group consisting essentially of proteases and GAGases and gelling the digested tissue by adjusting the pH of the submucosal tissue to about 6.0 to about 7.0. Typically the submucosal tissue is sterilized prior to use in cell culture applications.

In one preferred embodiment, a composition comprising fluidized vertebrate submucosa that has been treated with galactosidase to deplete the detectable levels of the Gal epitope is prepared by first treating the native submucosal tissue with galactosidase and then fluidizing the tissue. In particular, the submucosal tissue is prepared, in its native sheet-like configuration, and contacted with a solution containing galactosidase. The digestion is conducted for a time sufficient to reduce the Gal epitope content of the tissue, and preferably the submucosal tissue is enzymatically treated with galactosidase for a sufficient time to be substantially free of detectable amounts of the Gal epitope. After the tissue has been enzymatically digested to deplete the Gal epitope content, the tissue is repeatedly washed in saline or a suitable buffered solution to remove the cleaved epitope and the enzyme. The tissue is then fluidized by comminuting and/or enzymatic digestion as described above, and in U.S. Pat. No. 5,275,826.

EXAMPLE 1

The Presence of the Gal epitope in porcine submucosal tissue and its removal by enzymatic digestion.

Materials and Methods

Reagenits: Normal human serum (NHS) was prepared fresh from 4 individuals and pooled. Human serum albumin was purchased from Calbiochem. Goat anti-human IgG (Fc fragment) and antihuman IgM ($\mu$ chain specific) conjugated to horseradish peroxidase (HRP) were purchased from Bethyl Labs (Montgomery, Tex.). The lectin I-B4 (from *Griffontia simplicifolia*) HRP conjugate, α-galactosidase, and lipopolysaccharide from *E. coli* were purchased from Sigma (St. Louis, Mo.). Diaminobenzidine (DAB), the peroxidase substrate, was purchased from Vector Labs (Burlingame, Calif.). Complement C3a des-Arg radioimmunoassay kit was purchased from Amersham (Madison, Wis.). Phosphate buffered saline (PBS), pH 7.4 was prepared as needed.

Tissues: Six hydrated submucosal tissue specimens from six different pigs were prepared essentially as described in U.S. Pat. No. 4,902,508, and were supplied by Cook Biotech Inc. Fresh porcine liver was used as a positive control tissue. Samples were frozen in O.C.T.® embedding medium (Miles) as a cryoprotectant and stored at −70° C. until use. Cross-sectional slices of submucosal tissue (perpendicular to the tissue long axis) were cut on a cryomicrotome set to a thickness of 7 $\mu$m and mounted on poly-L-lysine coated slides.

Immunohistochemical staining: Slides were allowed to warm to room temperature (RT) and fixed in acetone for 3 min at 4° C. Nonspecific protein binding was blocked by incubating the slides in 2% human serum albumin for 20 min. Endogenous peroxidase activity was inhibited by incubating for 30 min in 0.45% (v/v) $H_2O_2$ in methanol. The slides were rinsed in PBS for 10 min between incubations. All incubations were performed at RT except as noted.

The conditions used to stain the prepared tissues for the Gal epitope are summarized in Table 1:

TABLE 1

| Condition | Block | 1° Stain | 2° Stain |
|---|---|---|---|
| 1 | none | I-B$_4$-HRP | none |
| 2 | none | NHS | anti-human IgG-HRP |
| 3 | none | NHS | anti-human IgM-HRP |
| 4 | NHS | I-B$_4$-HRP | none |
| 5 | I-B$_4$-HRP | NHS | anti-human IgG-HRP |
| 6 | I-B$_4$-HRP | NHS | anti-human IgM-HRP |
| 7 | α-galactosidase | I-B$_4$-HRP | none |

Conditions 1–3 are simple immunoperoxidase staining procedures. Direct staining with I-B$_4$, which specifically binds Galα (1,3)Gal, was utilized because no anti-lectin reagent was available. Under conditions 4–6 the tissue was first exposed to either the lectin-BRP or normal human serum, then followed through the normal staining procedure. In particular, tissues were blocked by incubation with lectin-HRP for 18 hr at RT, or serum for 1 hour at 37° C. followed by 18 hour at RT. In the case of lectin-HP blocking, the tissue was exposed to H$_2$O$_2$/methanol solution after lectin binding to inactivate both the endogenous peroxidases and the HRP bound to the lectin.

The blocked tissues were then incubated in serum for 1 hour at 37° C. followed by 18 hours at room temperature (condition 5 and 6), or lectin for 1 hour at room temperature, respectively (condition 4). Serum-stained tissues were incubated with anti-IgM or anti-IgG HP conjugate at RT for 1 hour (condition 2,3,5,6). For condition 7, α-galactosidase, which cleaves terminal α-galactosyl residues, was employed at 20 units/ml prior to lectin staining, the enzyme digested tissues were then incubated for 18 hr at RT. All tissues were incubated in peroxidase substrate (DAB) solution for 10 minutes and counterstained with hematoxylin for 10 seconds. Finally, the slides were dehydrated through a graded alcohol series and mounted with a coverslip. Positive staining appears black against a purple background.

Results

Ali submucosal tissue samples stained strongly positive for the Gal epitope with the I-B4 lectin and with human serum containing naturally occurring antibodies to the epitope. The epitope appears to be transmurally distributed throughout the submucosal tissue. The hepatic portal triads, which contain abundant endothelial cells, also stained strongly positive while the hepatocytes were moderately positive. Staining intensity was decreased with serum treatment prior to lectin-HRP, but was not entirely eliminated. These results indicate that the Gal epitopes were being at least partially masked by specific interaction with the serum components.

Submucosal tissue treated with serum and stained with anti-IgG appeared similar to the lectin-stained tissue, while blocking with lectin-HRP significantly decreased staining intensity. Submucosal tissue treated with serum and stained with anti-IgM appeared similar to the anti-IgG stained tissue.

Digestion with α-galactosidase significantly decreased staining of both submucosal tissue and liver by the I-B4 lectin (see α-Gal.+Lectin, Table 2).

A summary of the results is presented in Table 2:

TABLE 2

Different Degree of Immunohistochemical Staining on CBI SIS

| Condit No | Lectin | Anti-body + Anti-IgG | Anti-body + Anti-IgM | α-Gal. + Lectin | Lectin + Anti-body + Anti-IgG | Lectin + Anti-body + Anti-IgM | Anti-body + Lectin |
|---|---|---|---|---|---|---|---|
| 1 | +++ | +++ | +++ | + | ++ | ++ | ++ |
| 2 | +++ | +++ | +++ | − | ++ | ++ | ++ |
| 3 | +++ | ++++ | +++ | + | + | ++ | + |
| 4 | +++ | ++++ | +++ | + | ++ | ++ | ++ |
| 5 | +++ | ++++ | +++ | + | ++ | + | ++ |
| 6 | +++ | ++++ | ++++ | + | ++ | ++ | ++ |

Staining recorded as − = absent, + = weak, ++ to ++++ = increasing intensity

EXAMPLE 2

Submucosal Tissue's ability to Activate Complement

Complement activation assay: Plasma samples were collected from healthy laboratory staff The blood was drawn into EDTA (K$_3$) Venoject® tubes (Terumo Medical, Elkton, Md.) and centrifuged immediately at 1,500×g for 15 min at 4° C. The plasma was removed from the cells and used immediately.

50 mg pieces of hydrated porcine submucosal tissue (blotted to remove excess liquid) were incubated with 250 μl of plasma (normal or heat-inactivated) for 1 hour at 37° C. Samples from three different lots were prepared in duplicate. The plasma was then separated from the submucosal tissue and assayed in accordance with the manufacturer's instructions for human complement C3a. Each sample was run in triplicate. In addition, 80 μl of a 10 mg/ml solution of lipopolysaccharide from E coli (purchased from Sigma) was also incubated with 250 μl of plasma (3.2 mg/ml of plasma) as a positive control. Controls also consisted of plasma incubated without submucosal tissue at both RT, and at 37° C. for 1 hour.

Each lot of submucosal tissue was tested twice. Every sample was run in triplicate. Calculations were done in accordance with the manufacturer's instructions. The log concentration of the standards was plotted against the percent bound with Excel software. An exponential line equation was determined and the concentration of C3 a in each of the triplicates was determined. After taking into consideration the dilution step of the assay, the results for each sample were averaged and the standard deviation determined. The results presented are from one experiment; however, the assay was performed 5 times with different pools of plasma and the results were consistent. The results were compared for statistical significance with single factor ANOVA.

Results

| | |
|---|---|
| plasma incubated at room temperature for 1 hour | 154 ng/ml ± 13 |
| plasma incubated at 37° C. for 1 hour | 332 ng/ml ± 134 |
| plasma with lipopolysaccharide | >16,000 ng/ml |
| plasma with submucosal tissue lot 1, sample A | 191 ng/ml ± 9 |
| plasma with submucosal tissue lot 1, sample B | 354 ng/ml ± 170 |
| plasma with submucosal tissue lot 2, sample A | 234 ng/ml ± 14 |
| plasma with submucosal tissue lot 2, sample B | 249 ng/ml ± 113 |

-continued

Results

| | |
|---|---|
| plasma with submucosal tissue lot 3, sample A | 220 ng/ml ± 50 |
| plasma with submucosal tissue lot 3, sample B | 393 ng/ml ± 144 |

Average and standard deviation of all 6 tubes of:

| | |
|---|---|
| submucosal tissue 1 | 273 ng/ml ± 140 |
| submucosal tissue 2 | 241 ng/ml ± 72 |
| submucosal tissue 3 | 307 ng/ml ± 135 |

Average and standard deviation of all 18 tubes of submucosal tissue:

274 ng/ml±116

The results for the complement C3a assay, shown above, indicate that intestinal submucosa prepared in accordance with the procedures described in U.S. Pat. No. 4,902,508 (i.e., without treatment to remove the Gal epitope) does not produced significant complement activation in vitro. Neither of the negative control plasma samples produced significant complement activation in vitro, nor did the submucosal tissue treated samples, the differences between these three samples were not significantly different (p=0.15). The lipopolysaccharide (positive control) showed complement C3a concentration greater than 16,000 ng/ml, which was off the standard curve.

EXAMPLE 3

The use of Galα(1,3)Gal epitope depleted submucosal tissue as a cell growth substrate.

Material and Methods
  Cell lines
  Fetal rat keratinocytes (FR)
  Swiss 3T3 fibroblast cells (M)
  Procedure Hydrated submucosal tissue in sheet form was supplied by Cook Biotech Inc. The submucosal tissue was placed in a plastic holder to keep the tissue flat and ensure good contact of the cells with the tissue. The tissue was treated with α-galactosidase to remove the Gal epitope as follows: α-galactosidase was suspended in 3.5 M ammonium sulfate, 50 mM sodium acetate, pH 5.5 to a final concentration of 20 units/ml. The treatment solution (50 μl) was added to the well of submucosal tissue holder, and the submucosal tissue (50 mg) was incubated at room temperature overnight. Three samples of submucosal tissue were treated under the following conditions:

1. submucosal tissue incubated with α-galactosidase
  2. submucosal tissue incubated with 3.5 M ammonium sulfate, 50 mM sodium acetate, pH 5.5
  3. submucosal tissue incubated with water After incubating the tissues overnight, the tissue samples were rinsed with PBS followed by complete cell culture medium. A submucosal tissue holder was placed in each well of a 12-well plate, and 2 ml of complete culture medium was added to the well. 20,000 FR cells or 13,000 3T3 cells were seeded onto the submucosal side of the submucosal tissue in a total volume of 250 μl. The plate was placed in a 37° C. $CO_2$ incubator. At 48 hours and 1 week, samples were fixed in neutral buffered formalin for histologic evaluation (hematoxylin and eosin stained), or 2% glutaraldehyde in phosphate buffered saline for examination by scanning electron microscopy.

Results

FR cells grew and differentiated similarly on all submucosal tissue samples. There were more cells present at 1 week than after 48 hours. There were no significant differences observed between the three treated submucosal tissue substrates.

3T3 cells also grew and differentiated similarly on all 3 submucosal tissue substrates. There were more cells present at 1 week than after 48 hours. There were no significant differences observed between three treated submucosal tissue substrates.

What is claimed is:

1. A tissue graft composition comprising vertebrate submucosal tissue enzymatically treated to be substantially free of the Gal epitope.

2. The tissue graft composition of claim 1 wherein the submucosal tissue is a segment of intestinal submucosa comprising the tunica submucosa delamninated from the tunica muscularis and at least the luminal portion of the tunica mucosa of vertebrate intestine.

3. The tissue graft composition of claim 1 wherein the submucosal tissue is treated with galactosidase.

4. The tissue graft composition of claim 3, wherein the submucosal tissue is digested with an enzyme for a period of time sufficient to solubilize the tissue.

5. The tissue graft composition of claim 4 gelled to form a solid or semi-solid matrix suitable for culturing eukaryotic cells on the surface of the matrix.

6. A tissue graft construct comprising intestinal submucosa delaminated from the tunica muscularis and at least the luminal portion of the tunica mucosa of vertebrate intestine and incubated with galactosidase for a sufficient amount of time to be substantially free of the Gal epitope.

7. A composition for supporting the growth of a cell population, said composition comprising submucosal tissue that has been fluidized by enzymatically digesting the tissue with an enzyme selected from the group consisting essentially of proteases and GAGases;
  enzymatically treated with galactosidase to remove substantially all detectable amounts of the Gal epitope; and
  gelled by adjusting the pH of a solution of enzymatically digested submucosal tissue to about 6.0 to about 7.0.

* * * * *